(12) United States Patent
Tremblay et al.

(10) Patent No.: US 9,480,765 B2
(45) Date of Patent: Nov. 1, 2016

(54) STERILIZATION APPARATUS

(71) Applicant: TSO3 INC., Quebec (CA)

(72) Inventors: Bruno Tremblay, Quebec (CA); Jean-Martin Vallieres, Quebec (CA)

(73) Assignee: TSO3 INC., Quebec (CA)

( * ) Notice: Subject to any disclaimer, the term of this patent is extended or adjusted under 35 U.S.C. 154(b) by 659 days.

(21) Appl. No.: 13/780,464

(22) Filed: Feb. 28, 2013

(65) Prior Publication Data

US 2013/0236363 A1 Sep. 12, 2013

Related U.S. Application Data

(63) Continuation of application No. 12/893,742, filed on Sep. 29, 2010, now Pat. No. 9,101,679.

(60) Provisional application No. 61/247,197, filed on Sep. 30, 2009.

(51) Int. Cl.
*A61L 2/20* (2006.01)
*B65D 23/00* (2006.01)

(52) U.S. Cl.
CPC ............ *A61L 2/208* (2013.01); *A61L 2/20* (2013.01); *A61L 2/202* (2013.01); *B65D 23/001* (2013.01);
(Continued)

(58) Field of Classification Search
CPC ........... A61L 2/16; A61L 2/18; A61L 2/186; A61L 2/20; A61L 2/202; A61L 2/208; A61L 2/22; A61L 2/24; A61L 2/26
See application file for complete search history.

(56) References Cited

U.S. PATENT DOCUMENTS 3,717,274 A 2/1973 Wingardh
3,880,011 A 4/1975 Johnson
(Continued)

FOREIGN PATENT DOCUMENTS

EP 0298694 1/1989
EP 1121942 8/2001
(Continued)

OTHER PUBLICATIONS

English Translation of Japanese Patent Application No. 2013-083152 Office Action dated Oct. 21, 2014.
(Continued)

*Primary Examiner* — Timothy Cleveland
(74) *Attorney, Agent, or Firm* — Mark F. Vickers; Borden Ladner Gervais LLP

(57) ABSTRACT

A hydrogen peroxide delivery system for a sterilizer having a hydrogen peroxide injection unit and a housing is disclosed. The system includes a cradle for supporting a hydrogen peroxide solution container, a drainage arrangement for aspirating the hydrogen peroxide solution from the container, and a delivery arrangement for supplying the aspirated hydrogen peroxide solution to the hydrogen peroxide injection unit. The drainage arrangement includes a needle for penetrating a seal on the container and extending into the hydrogen peroxide solution in the container. A needle drive moves the needle from an at rest position, wherein the needle is retracted to allow insertion of a new hydrogen peroxide container into the cradle, to a penetrating position wherein the needle penetrates the seal of the container and extends all the way to the bottom of the container to ensure complete drainage of the hydrogen peroxide solution from the container.

22 Claims, 12 Drawing Sheets

(52) U.S. Cl.
CPC ....... *A61L 2202/122* (2013.01); *A61L 2202/13* (2013.01); *A61L 2202/14* (2013.01); *A61L 2202/24* (2013.01)

(56) References Cited

U.S. PATENT DOCUMENTS

| | | | |
|---|---|---|---|
| 3,978,232 A | | 8/1976 | Dodsworth et al. |
| 4,082,200 A | * | 4/1978 | Guest .................. B65D 23/001 215/12.1 |
| 4,434,820 A | | 3/1984 | Glass |
| 4,458,348 A | | 7/1984 | Fukuda |
| 4,548,348 A | | 10/1985 | Clements |
| 4,642,165 A | | 2/1987 | Bier |
| 4,838,887 A | | 6/1989 | Idriss |
| 4,952,370 A | | 8/1990 | Cummings |
| 4,956,145 A | | 9/1990 | Cummings |
| 5,115,792 A | | 5/1992 | Fukui |
| 5,122,344 A | | 6/1992 | Schmoegner |
| 5,445,792 A | | 8/1995 | Rickloff |
| 5,508,009 A | | 4/1996 | Rickloff et al. |
| 5,556,607 A | | 9/1996 | Childers |
| 5,644,093 A | * | 7/1997 | Wright ................. G01D 11/245 248/205.3 |
| 5,700,426 A | | 12/1997 | Schmitthaeusler |
| 6,070,761 A | | 6/2000 | Bloom |
| 6,096,266 A | | 8/2000 | Duroselle |
| 6,363,802 B1 | * | 4/2002 | Grippo ............... G01N 35/1011 73/864.24 |
| 6,488,650 B1 | | 12/2002 | Epstein |
| 6,699,434 B1 | | 3/2004 | Lukasik et al. |
| 7,048,887 B2 | | 5/2006 | Frost et al. |
| 7,186,371 B1 | | 3/2007 | Watling |
| 2003/0066346 A1 | | 4/2003 | Goloby |
| 2004/0022673 A1 | | 2/2004 | Protic |
| 2004/0146427 A1 | | 7/2004 | Awakowicz et al. |
| 2007/0014686 A1 | | 1/2007 | Arnold et al. |
| 2007/0020141 A1 | | 1/2007 | Chiffon et al. |
| 2007/0098591 A1 | | 5/2007 | Frinke |
| 2007/0258855 A1 | | 11/2007 | Turcot |
| 2008/0233002 A1 | | 9/2008 | Mizuno |
| 2011/0176959 A1 | | 7/2011 | Ko |

FOREIGN PATENT DOCUMENTS

| | | | | |
|---|---|---|---|---|
| EP | 1177986 | | 2/2002 | |
| EP | 1736175 | | 12/2006 | |
| FR | 2852849 | | 10/2004 | |
| GB | 2264936 A | * | 9/1993 | ............... A61L 2/00 |
| JP | 54-163993 | | 11/1979 | |
| JP | 56-064639 A | | 6/1981 | |
| JP | 63-246676 A | | 10/1988 | |
| JP | 01-274765 A | | 11/1989 | |
| JP | 04-087987 A | | 3/1992 | |
| JP | 04-114897 A | | 4/1992 | |
| JP | 04-054698 | | 5/1992 | |
| JP | 08-054400 A | | 2/1996 | |
| JP | 08-505787 | | 6/1996 | |
| JP | 08-238305 A | | 9/1996 | |
| JP | 08-285658 A | | 11/1996 | |
| JP | 2780228 | | 7/1998 | |
| JP | 3182658 | | 7/2001 | |
| JP | 2001-289687 | | 10/2001 | |
| JP | 2002-206655 | | 7/2002 | |
| JP | 2002-263174 A | | 9/2002 | |
| JP | 2002-272821 A | | 9/2002 | |
| JP | 2002-360672 | | 12/2002 | |
| JP | 2002-360673 A | | 12/2002 | |
| JP | 2003-095392 A | | 4/2003 | |
| JP | 2004-066236 A | | 3/2004 | |
| JP | 2004-160168 A | | 6/2004 | |
| JP | 2005-521518 A | | 7/2005 | |
| JP | 2006-036343 | | 2/2006 | |
| JP | 2006-110349 A | | 4/2006 | |
| JP | 2006-158958 A | | 6/2006 | |
| JP | 2006-204889 A | | 8/2006 | |
| JP | 2006-305379 | | 11/2006 | |
| JP | 2006-320613 A | | 11/2006 | |
| JP | 2007-518954 A | | 7/2007 | |
| JP | 2007-521118 | | 8/2007 | |
| JP | 2008-178479 | | 8/2008 | |
| JP | 2008-200511 | | 9/2008 | |
| JP | 2009-501631 A | | 1/2009 | |
| JP | 2009-535215 A | | 10/2009 | |
| JP | 2009-542333 A | | 12/2009 | |
| JP | 2009-545496 A | | 12/2009 | |
| JP | 2010-051692 A | | 3/2010 | |
| JP | 2010-532198 A | | 10/2010 | |
| JP | 2010-533030 A | | 10/2010 | |
| WO | 89/06140 | | 7/1989 | |
| WO | 93/17726 | | 9/1993 | |
| WO | 94/07544 A1 | | 4/1994 | |
| WO | 0002595 | | 1/2000 | |
| WO | 00/55070 A1 | | 9/2000 | |
| WO | 2005094907 A1 | | 10/2005 | |
| WO | 2009/008755 | | 1/2009 | |
| WO | 2009005252 | | 1/2009 | |

OTHER PUBLICATIONS

English Translation of Japanese Patent Application No. 2013-083238 Office Action dated Oct. 21, 2014.
English Translation of Japanese Patent Application No. 2013-083142 Office Action dated Sep. 30, 2014.
English Translation of Japanese Patent Application No. 2013-083154 Office Action dated Oct. 21, 2014.
English Translation of Japanese Patent Application No. 2013-083229 Office Action dated Oct. 21, 2014.
English Translation of Japanese Patent Application No. 2013-083146 Office Action dated Oct. 21, 2014.
European Patent Application No. 13158395.7-1356 Office Action dated Nov. 19, 2014.
European Patent Application No. 13158399.9, Office Action dated Mar. 4, 2014.
European Patent Application No. 13158381.7, Office Action dated Feb. 11, 2014.
European Patent Application No. 13158404.7, Office Action dated Feb. 11, 2014.
European Patent Application No. 13158395.7, Office Action dated Feb. 11, 2014.
Favero, "Disinfection and sterilization in healthcare facilities", Chapter 2, Biocides Development, Ed. Zhu ACS Symposium Series, American Chemical Society, Washington DC, Sep. 7, 2007, pp. 31-50.
McDonnell, "Peroxygens and other forms of oxygen: their use for effective cleaning, disinfection, and sterilization", Chapter 13, New Biocides Development, Ed. Zhu, ACS Symposium Series, American Chemical Society, Washington, DC., Sep. 7, 2007, pp. 292-308.
Kulla et al., "Sterilizing combination products using oxides of nitrogen", Medical Device and Diagnostic Industry, Mar. 2009, 6 pages.
International Patent Application No. PCT/CA2010/001518, International Search Report dated Jan. 13, 2011.
Extended European Search Report dated May 31, 2013, European Patent Application No. 13158399.9.
Extended European Search Report dated May 2, 2013, European Patent Application No. 13158378.3.
Extended European Search Report dated May 7, 2013, European Patent Application No. 13158381.7.
Extended European Search Report dated May 7, 2013, European Patent Application No. 13158395.7.
Extended European Search Report dated May 7, 2013, European Patent Application No. 13158388.2.
Extended European Search Report dated May 7, 2013, European Patent Application No. 13158404.7.
Extended European Search Report dated May 31, 2013, European Patent Application No. 10819766.6.
Patent Examination Report dated Apr. 5, 2013, Australian Patent Application No. 2013201176.

(56) References Cited

OTHER PUBLICATIONS

Patent Examination Report dated Jun. 18, 2013, Australian Patent Application No. 2013201199.
English Abstract of Japanese Patent Application No. 05-504285, Jul. 8, 1993.
English Abstract of Japanese Patent Application No. 08-504612, May 21, 1996.
U.S. Appl. No. 12/893,742, Notice of Allowance dated Jul. 1, 2015.
U.S. Appl. No. 13/779,193, Office Action dated Jul. 9, 2015.
Japanese Patent Application No. 2013-083142, English Translation of Office Action dated May 26, 2015.
U.S. Appl. No. 13/779,132 Office Action dated Jul. 15, 2015.
U.S. Appl. No. 12/893,742, Office Action dated Jun. 26, 2014.
English Translation of Japanese Patent Application No. 2012-531191, Office Action dated Jul. 2, 2013.
Japanese Patent Application No. 2013-083142, Notice of Allowance dated Oct. 27, 2015, English translation dated Dec. 27, 2015.
European Patent Application No. 13158395.7, Intent to Grant dated Nov. 24, 2015.
English Abstract of Japanese Patent Application No. 06-510932, published as WO 93/17726, published Sep. 16, 1993.
U.S. Appl. No. 13/779,193, Office Action dated Dec. 10, 2015.
U.S. Appl. No. 13/779,168, Office Action dated Dec. 15, 2015.
European Patent Application No. 16160873.2, extended European Search Report dated May 9, 2016.

\* cited by examiner

CON(C3) ←──── 
(PA-01) UPPER POSITION (S8)
(PA-01) LOWER POSITION (S9)
COMPARTMENT STATUS (S7)
H2O2 COMPARTMENT STATUS (S6)
COMPARTMENT LOCK STATUS (S12)
SLIDE DOOR (S13)
BARATRON VACUUM SWITCH
CPS-7 OPTIONAL INPUT
CPS-6 OPTIONAL INPUT
CPS-5 OPTIONAL INPUT
COOLANT FLOW SENSOR (COOLING)
REFRIDGERANT LOW PRESSURE (COOLING)
OXYGEN HIGH PRESSURE SENSOR
OXYGEN LOW PRESSURE SENSOR
OZONER UNIT HIGH PRESSURE
DOOR CLOSED LOWER SENSOR (S2)
DOOR CLOSED UPPER SENSOR (S1)
DOOR LOCKED SENSOR (S4)
DOOR UNLOCKED SENSOR (S3)
PRINTER OFFLINE SENSOR
PRINTER OUT OF PAPER SENSOR
OZONE MONITOR FAILURE SENSOR
CHAMBER PRESSURE SENSOR AT TEMPERATURE (PT-01)
CHAMBER PRESSURE SENSOR HEATER FAILURE (PT-01)
AUXILLIARY ALARM INPUT (PEB-1)
AIR COMPRESSOR PRESSURE STATUS (PS-03)
H2O2 27mm LEVEL SENSOR (S10) OR SONIC ALTERNATE SYS.
H2O2 15mm LEVEL SENSOR (S11) OR FOAM DETECTOR ALT.
SYS

FIG. 9C

STERILIZATION APPARATUS

CROSS REFERENCE TO RELATED APPLICATIONS

This application is a continuation application of U.S. application Ser. No. 12/893,742, filed Sep. 29, 2010 and entitled STERILIZATION METHOD AND APPARATUS, which claims priority from U.S. Provisional Application Ser. No. 61/247,197, filed Sep. 30, 2009 and entitled STERILIZATION METHOD AND APPARATUS, the contents of which are incorporated into the present application in their entirety.

FIELD OF THE INVENTION

The present invention relates generally to sterilization apparatus. More particularly, the present invention relates to a hydrogen peroxide delivery system for a sterilization apparatus using gaseous hydrogen peroxide under vacuum.

BACKGROUND OF THE INVENTION

Sterilization is the destruction of any virus, bacteria, fungus or other micro-organism, whether in a vegetative or in a dormant spore state and is defined by a $10^{-6}$ reduction in the level of bacteria. Conventional sterile processing procedures for medical instruments involve high temperature (such as steam and dry heat units) or chemicals (such as ethylene oxide gas, hydrogen peroxide, or ozone).

Sterilization methods and apparatus using gaseous sterilants are well known. Sterilizers using hydrogen peroxide as the sterilant are widely used. The hydrogen peroxide is generally supplied as an aqueous solution and evaporated prior to injection into a sterilization chamber of the sterilizer, by heating of the solution, or by applying a vacuum to the sterilization chamber, or both. After evaporation of the solution, the sterilization atmosphere in the sterilization chamber includes water vapor and hydrogen peroxide gas. It is a disadvantage of this process that the water vapor tends to condensate on articles in the chamber as the sterilization proceeds. The resulting layer of water condensate on the articles to be sterilized interferes with the sterilizing action of the hydrogen peroxide. Numerous apparatus and process modifications have been developed to address this problem, all of which are aimed at limiting the relative humidity in the sterilization atmosphere during the sterilization process. However, these modifications invariably increase operating cost and/or sterilization cycle times.

Sterilizers using ozone containing gas as the sterilant are also known. The ozone gas is generally produced externally to the sterilization chamber and supplied into the chamber under vacuum to increase penetration of the sterilant gas into restricted spaces on the articles to be sterilized. In order to improve the sterilization effect of ozone gas, the sterilization atmosphere is generally humidified with water prior to the injection of ozone gas into the sterilization chamber. However, the amount of ozone gas needed is relatively high (85 mg/l) and the sterilization cycle times are relatively long, making ozone based sterilization processes comparatively expensive. Furthermore, many articles to be sterilized are damaged by the high levels of ozone required to achieve complete sterilization and can therefore not be sterilized in an ozone sterilization process.

Sterilization processes using both hydrogen peroxide gas and ozone gas have been used, but with unsatisfactory results especially with respect to the sterilization of articles with long internal lumens, such as gastroscopes and colonoscopes, and with respect to cycle times and sterilization cost. Although ozone based processes are satisfactory with respect to sterilization of articles with long lumens, material compatibility represents a problem. Hydrogen peroxide based processes are generally unsatisfactory regarding the sterilization of long lumens.

Therefore, a method and apparatus is desired which would address at least one of the disadvantages of known sterilization processes using gaseous sterilants.

SUMMARY OF THE INVENTION

It is an object of the present disclosure to provide a system to obviate or mitigate at least one disadvantage of previous sterilant delivery systems.

In one aspect, the disclosure provides a hydrogen peroxide delivery system for a sterilizer having a hydrogen peroxide injection unit and a housing. The system includes a cradle for supporting a sealed hydrogen peroxide solution container within the housing, a drainage arrangement connected with the cradle for aspirating the hydrogen peroxide solution from the container, and a delivery arrangement connected with the drainage arrangement for supplying the aspirated hydrogen peroxide solution to the hydrogen peroxide injection unit.

In a further aspect, the drainage arrangement includes a drainage needle connected with the delivery arrangement for penetrating a seal on the container and extending into the hydrogen peroxide solution in the container, and a needle drive for moving the needle from an at rest position, wherein the needle is retracted to allow insertion of a new hydrogen peroxide container into the cradle, to a penetrating position wherein the needle penetrates the seal of the container and extends into the hydrogen peroxide solution in the container. Preferably, the needle extends all the way to a bottom of the container in the penetrating position. Most preferably, the needle drive is reciprocatable.

In another aspect, the disclosure provides a hydrogen peroxide delivery system, wherein the container includes a stand for supporting a hydrogen peroxide solution container in an upright position within the housing. Preferably, the needle drive is reciprocatable for moving the needle from an at rest position, wherein the needle is retracted to allow insertion of a new hydrogen peroxide container in the stand, to a penetrating position wherein the needle penetrates the seal of the container and extends into the hydrogen peroxide solution in the container, the needle extending all the way to a bottom of the container in the penetrating position.

In still a further aspect, the delivery system of the present disclosure uses a hydrogen peroxide solution container with a conical bottom, whereby the conical bottom of the container is centered with an axis of the drainage needle for aligning a tip of the needle with the lowest point of the bottom.

In yet another aspect, the present disclosure provides a sealed hydrogen peroxide solution container including a hollow body with a top end including a sealed fill and drainage opening, a side wall and a conical bottom, a stand for maintaining the container in an upright position on a flat horizontal surface prior to insertion into the cradle and a connecting arrangement for connecting the stand to the body, whereby the bottom of the container is conical to ensure any residual hydrogen peroxide solution collects at a lowest point of the bottom. Preferably, the stand is snap fitted onto the hollow body. More preferably, the container includes an external recess in the side wall of the body and the stand is cup-shaped and has a radially inwardly extending tab for engagement with the recess to provide a snap fit connection of the stand to the body. Most preferably, the recess is a circumferentially extending, continuous groove and the stand includes at least two tabs for engagement of the groove.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the sterilizer, method and delivery system of this disclosure will now be described, by way of example only, with reference to the attached Figures, wherein:

FIGS. 9a, 9b, and 9c, also referenced collectively herein as FIG. 9, is a schematic diagram of an exemplary control system;

FIG. 10b is a cross-sectional view of the container of FIG. 10a;

FIG. 10c is a side elevational view of the container of FIG. 10a; and

DETAILED DESCRIPTION OF THE PREFERRED EMBODIMENT

Generally, the present disclosure provides a hydrogen peroxide delivery system for use in methods and systems for sterilization of an article in a sterilization atmosphere by adding evaporated hydrogen peroxide.

Figure 3:
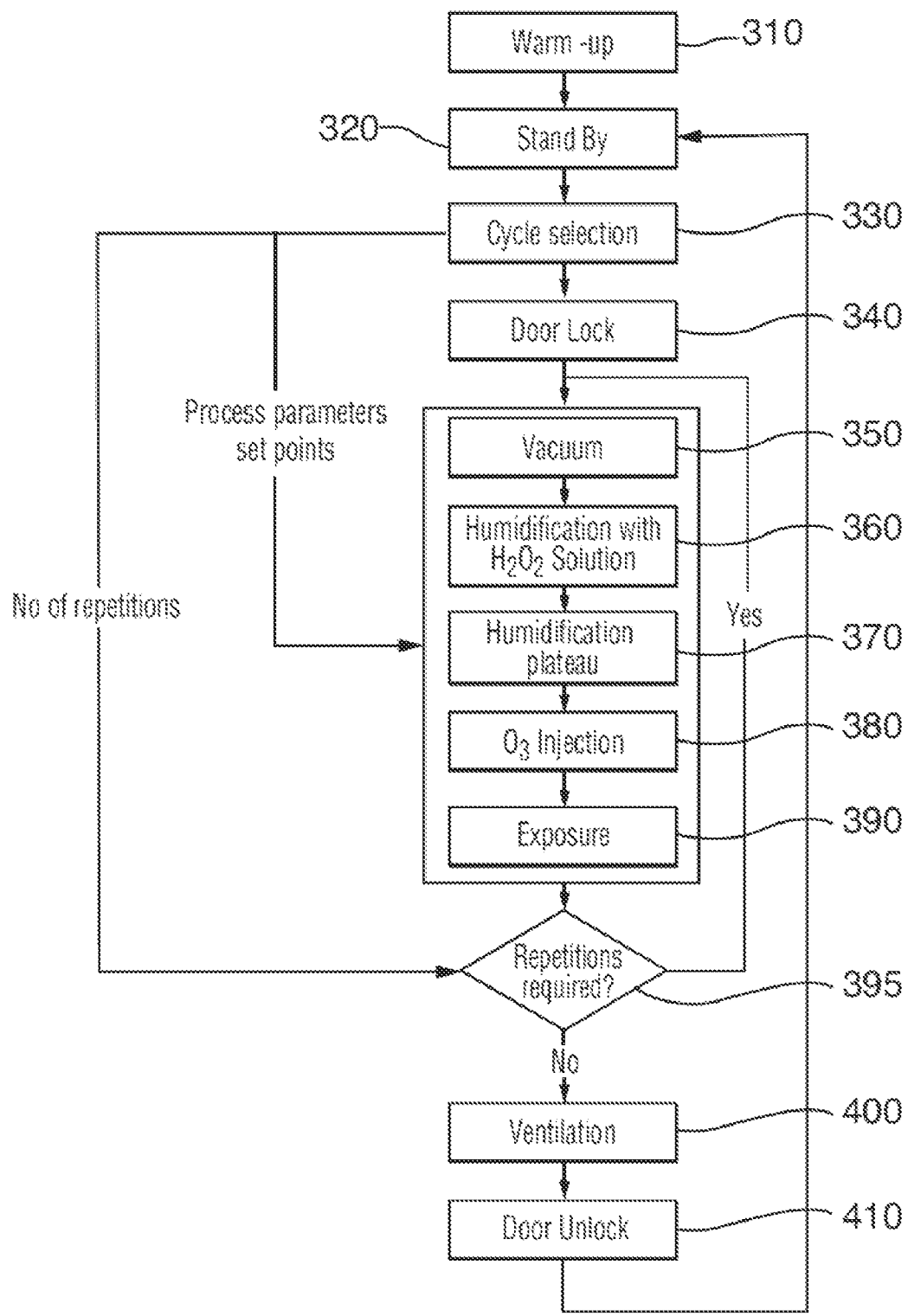
FIG. 3 is a flow diagram of a preferred sterilization method.
Figure 4:
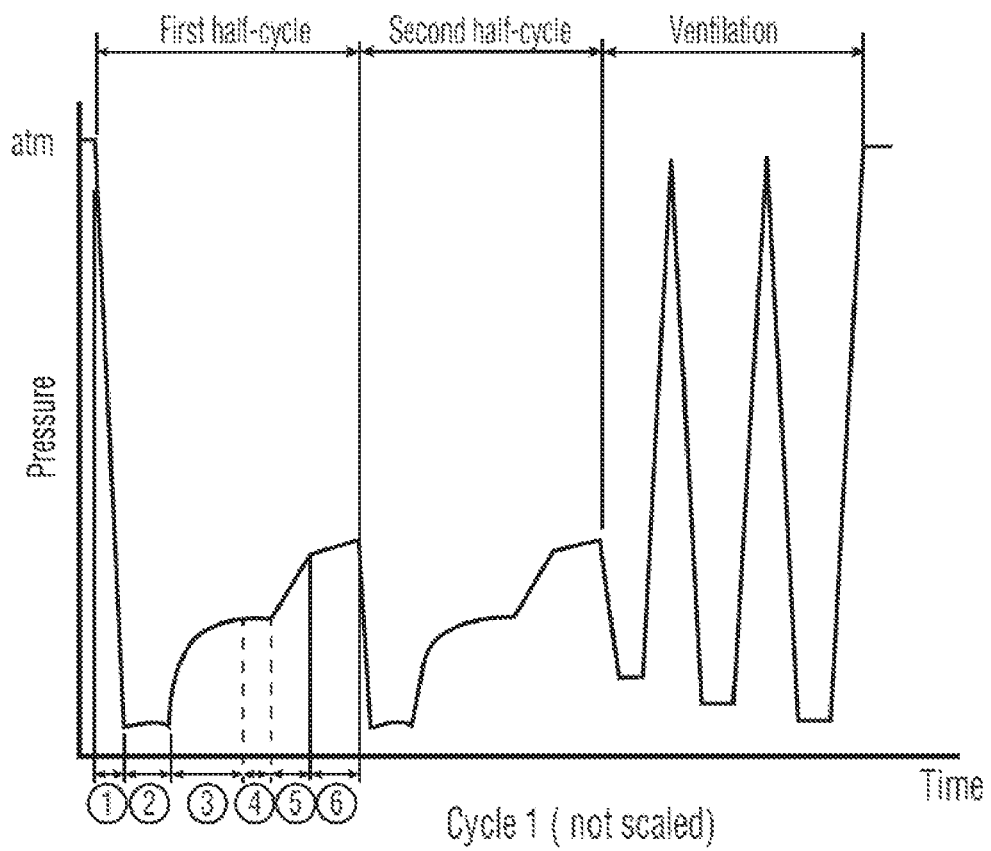
FIG. 4 is a graph illustrating a first exemplary sterilization cycle.
Figure 5:
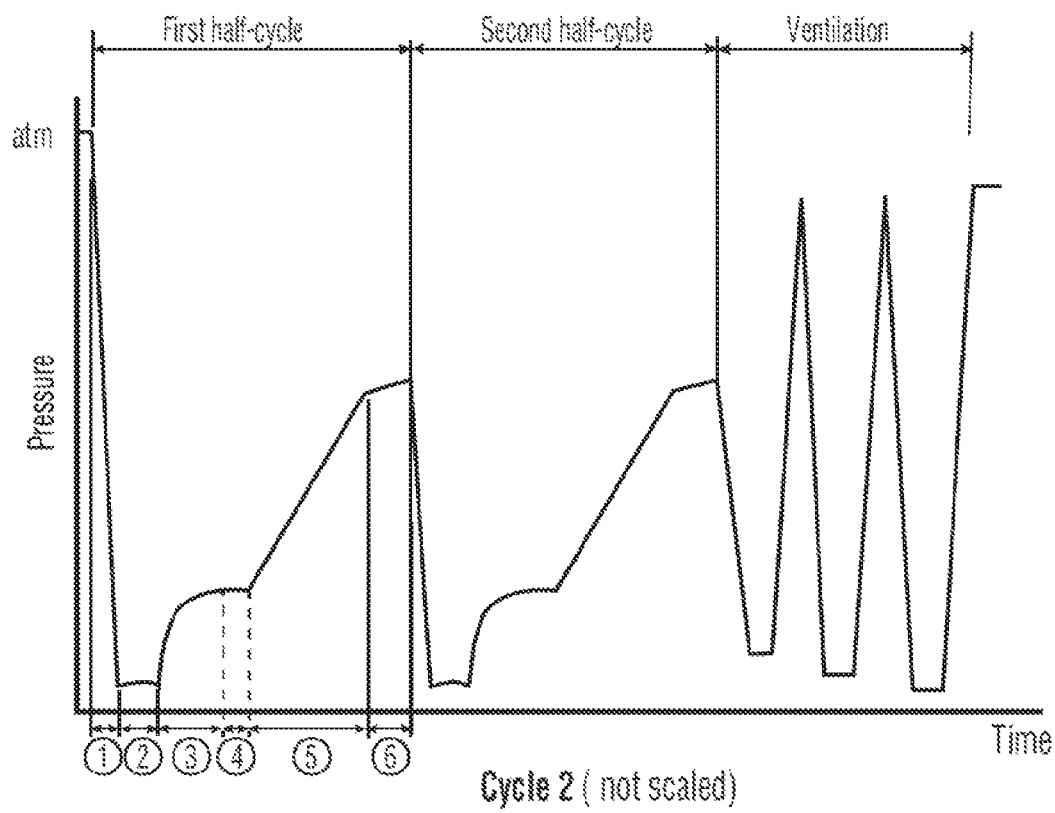
FIG. 5 is a graph illustrating a second exemplary sterilization cycle.
Figure 6:
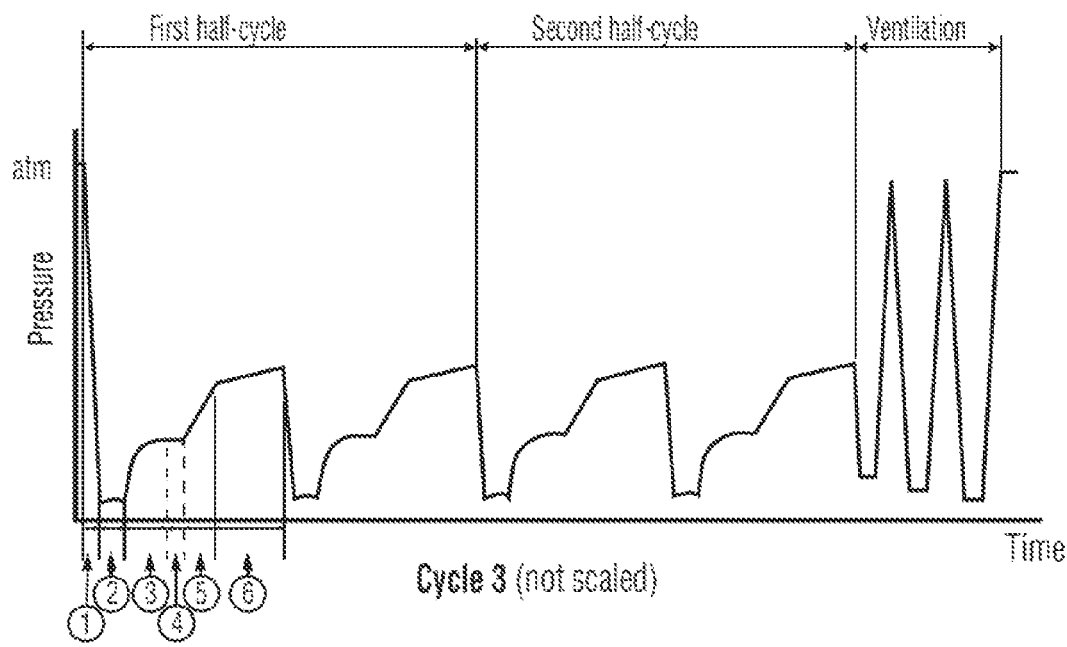
FIG. 6 is a graph illustrating a third exemplary sterilization cycle.

The delivery system can be used, for example, in a method of sterilizing an article by exposure to hydrogen peroxide and ozone, as illustrated in the flow diagram of FIG. 3 and the cycle graphs of FIGS. 4 to 6. In that method, the article is exposed under vacuum first to an evaporated aqueous solution of hydrogen peroxide and subsequently to an ozone containing gas. Preferably, the sterilization process is achieved while the chamber remains sealed and under vacuum. For this purpose, the chamber is initially evacuated to a first vacuum pressure sufficient to cause evaporation of the aqueous hydrogen peroxide at the temperature of the chamber atmosphere. The chamber is then sealed and hydrogen peroxide and ozone containing gas are sequentially added to the chamber and maintained in the chamber for a preselected exposure time. All removal of any components in the sterilization atmosphere is stopped during addition of the sterilants and for the duration of the exposure time. The aqueous hydrogen peroxide solution is evaporated and directly injected into the sterilization chamber without any measures to reduce the water vapor content.

The delivery system can be used in an exemplary sterilizer as illustrated schematically in FIG. 1, which sterilizer operates generally in the following manner. An article to be sterilized (not shown) is placed into a sterilization chamber 10 and the chamber is sealed. A vacuum is applied to the chamber 10. Evaporated hydrogen peroxide solution is supplied into the sterilization chamber 10 from a delivery unit 30 (see FIG. 8), which will be discussed in more detail below. The evaporated hydrogen peroxide supplied into the chamber provides a partial sterilization of the article. Medical quality oxygen is subjected in an ozone generator 22 to an electrical field, which converts the oxygen into ozone containing gas. The ozone containing gas is then fed into the chamber 10, which has been humidified by the injection of the evaporated hydrogen peroxide solution and the decomposition of the hydrogen peroxide into free radicals (hydroxyls), water and oxygen. The ozone containing gas finishes the sterilization of the article. Remaining sterilant gases are subsequently decomposed into water and oxygen using a catalyst 52. The only residues left at the end of the sterilization cycle are oxygen and clean water.

The use of a delivery system in accordance with the present disclosure allows for a hydrogen peroxide sterilization method to be carried out without the handling of dangerous gas cylinders, and poses no threat to the environment or the user's health.

Figure 1:
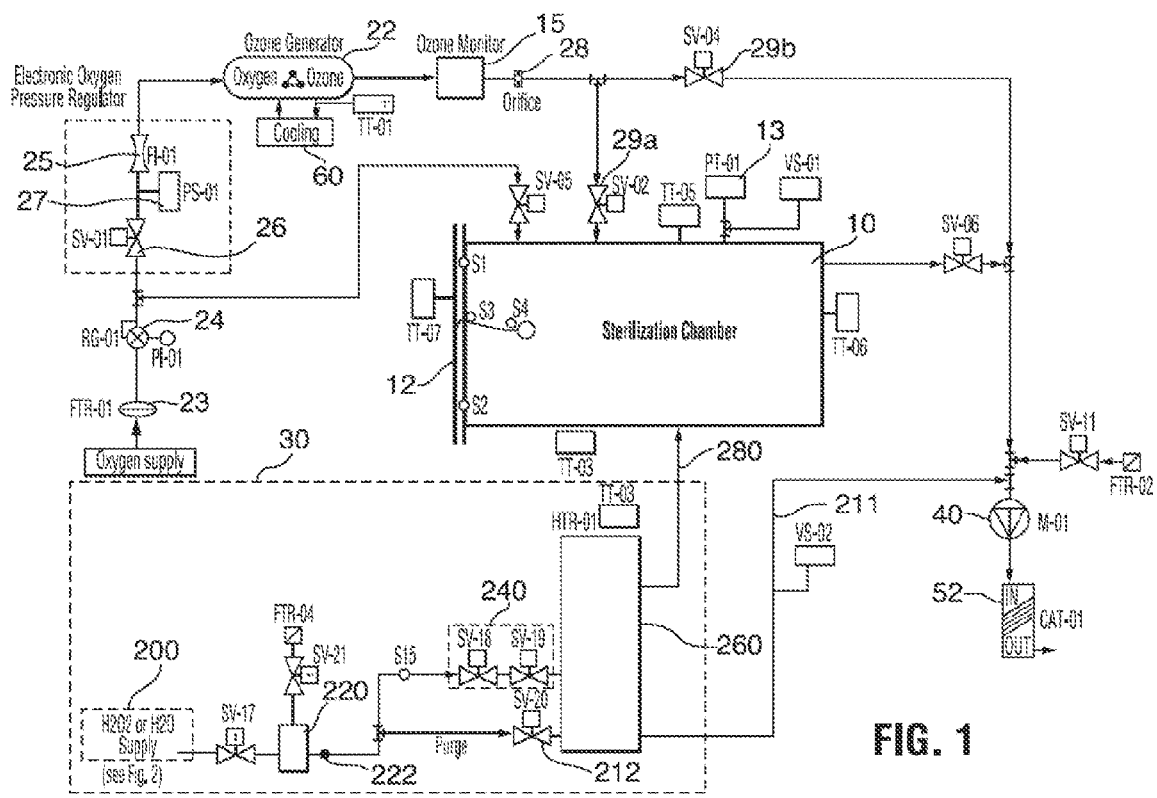
FIG. 1 shows a schematic diagram of an apparatus in accordance with the disclosure, the illustrated parts of the apparatus being listed in Table III.

An exemplary sterilization apparatus in connection with which the delivery system of the present disclosure can be used is illustrated schematically in FIG. 1. The exemplary apparatus includes a sterilization chamber 10 which can be sealed to contain a vacuum. This is achieved with an access door 12, which can be selectively opened for access into the chamber and which seals the chamber in the closed condition. The apparatus further includes an ozone generator 22 for supplying ozone-containing gas to the sterilization chamber, a hydrogen peroxide delivery unit 30 for supplying evaporated hydrogen peroxide to the sterilization chamber 10, and a vacuum pump 40 (CM-005-052 TSO3, Inc.). The vacuum pump 40 is used for the application of a sufficient vacuum to the sterilization chamber 10 to increase the penetration of the sterilizing gas and to be able to generate evaporated hydrogen peroxide solution at a temperature below the temperature inside the sterilization chamber. The vacuum pump 40 in the preferred embodiment is capable of producing a sufficient vacuum in the sterilization chamber to lower the boiling point of water in the chamber below the actual temperature of the atmosphere in the chamber. In the preferred apparatus, the vacuum pump is capable of producing a vacuum of 1 Torr (1.33 mbar). For economic and practical reasons, it is preferred to use a catalyst for decomposition of the sterilant in the sterilization gas exhausted from the sterilization chamber 10. The catalyst destroys hydrogen peroxide on contact and retransforms it into oxygen and water with a certain amount of heat being produced. Catalysts of this type and their manufacture are well known to the person skilled in the art and need not be described in detail herein. Furthermore, other means for destroying hydrogen peroxide contained in the sterilization gas will be readily apparent to a person skilled in the art. For example, the gas can be heated for a preselected time to a temperature at which the sterilant decomposition is accelerated, for example, to 300° C. for a period of 3 seconds.

The hydrogen peroxide delivery unit 30 includes a reservoir 220 (AM-213-010, TSO₃ Inc.), a metering unit 240, and an evaporator unit 260 (FM-213-003, TSO₃ Inc.) directly connected to the sterilization chamber 10 through a conduit 280. (AM-213-003, TSO₃ Inc.) The reservoir 220 is equipped with a level sensor 222 to always ensure a sufficiently high level of hydrogen peroxide for the execution of another sterilization cycle. A hydrogen peroxide solution (3-59%) is supplied to the reservoir from a hydrogen peroxide supply unit 200 (see FIG. 7), which will be discussed in more detail below. The hydrogen peroxide solution is supplied into the supply unit 200 from a sealed hydrogen peroxide solution container, in this embodiment a bottle 180 (see FIG. 7). The evaporated hydrogen peroxide solution produced in the evaporator unit 260 directly enters the sterilization chamber 10 with no intermediate flow restriction or valve. The evaporator unit is preferably equipped with a heating device (not shown) that maintains the temperature of the hydrogen peroxide solution sufficiently high to achieve a higher evaporation rate and prevent freezing of the solution.

The ozone generator 22 (OZ, model 14 a, TSO₃ Inc.) is of the corona discharge type and is cooled to decrease the ozone decomposition rate, all of which is well known in the art.

The vacuum in the sterilization chamber 10 is produced by way of the vacuum pump 40 and the sterilization chamber drainage valve 44.

Valves 29a and 29b are Teflon solenoid valves (CM-900-156, TSO3 Inc.) Valve 26 and vacuum valve 44 are solenoid valves (CM-015-004, TSO3 Inc.).

The preferred ozone generator used in the process and apparatus of the invention is a generator of the corona discharge type, which is well known to the person skilled in the art and need not be further described herein.

Operation

An exemplary sterilization method includes the following general steps as illustrated by the flow chart of FIG. 3. Articles to be sterilized, such as medical instruments, can be placed directly into the sterilization chamber, but are preferably sealed in sterile packaging containers, sterile wraps or pouches such as generally used in the hospital environment and then placed into the sterilization chamber.

After insertion of the article to be sterilized has been placed into the sterilization chamber in step 320, the door of the sterilization chamber is closed and the chamber sealed in step 340 and a vacuum is applied to the sterilization chamber in step 350 until a first pressure of 1 Torr (1.33 mbar) is reached in the chamber. The sterilization chamber walls have preferably been preheated in a warm-up step 310 to a temperature of 40° C. Evaporated hydrogen peroxide solution is admitted into the sterilization chamber in humidification step 360 to partially sterilize and humidify the chamber contents. The injection of evaporated hydrogen peroxide solution is stopped once a pressure increase of 19 Torr has been achieved in the chamber. The chamber can be maintained sealed for a first exposure period 370 (preferably 2 minutes) during which the hydrogen peroxide at least partially decomposes into free radicals, water and oxygen. This exposure period can also be omitted. An ozone containing gas, preferably in the form of a mixture of dry ozone and oxygen is then supplied to the chamber in the ozone injection step 380 and the chamber maintained sealed for a preselected second exposure period 390. No humidification of the ozone containing gas is carried out, or is even necessary, since the chamber atmosphere has been humidified by the hydrogen peroxide solution. Between the application of the vacuum, before the hydrogen peroxide evaporation step, and the end of the second exposure period, all removal of any sterilization atmosphere components is interrupted so that none of the components of the atmosphere are removed before the end of the second exposure period. The steps of vacuum application, hydrogen peroxide injection with first exposure period and ozone gas injection with second exposure period, are preferably repeated at least once, the number of repetitions being determined in step 395 on the basis of the cycle chosen previously in step 330. To remove all remaining sterilants from the sterilization chamber 10 after the sterilization cycle is completed a ventilation phase 400 is commenced, which preferably includes multiple cycles of evacuation of the chamber and flushing with oxygen. After the ventilation phase 400, the door is unlocked in step 410 and the sterilized articles can be taken from the chamber. The temperature of the floor and door of the chamber and of the evaporator unit is preferably controlled throughout the sterilization process.

In an exemplary sterilization apparatus, the user has the choice of multiple different sterilization cycles. In a preferred method, the user can choose in cycle selection step 330 of the process among three cycles which have the respective characteristics shown in Table 1 and discussed below.

TABLE I

| | Cycle phases | | |
|---|---|---|---|
| | Cycle 1 | Cycle 2 | Cycle 3 |
| Vacuum | 1 Torr | 1 Torr | 1 Torr |
| Humidification with 50% H202 solution | 20 Torr | 20 Torr | 20 Torr |
| Humidification plateau (optional) | 2 min | 2 min | 2 min |
| 03 Injection | 2 mg/1 | 10 mg/L | 3 mg/L |
| Exposure | 5 min | 5 min | 10 min |
| Nb of repetition(s) | 2 | 2 | 4 |
| Approx. Cycle duration | 46 min | 56 min | 100 min |

Cycle 1—Surface sterilization of devices having low compatibility with ozone, hinged devices and short flexible endoscopes (1 mm x 85 cm). (Ex. Cameras, cables, paddles, forceps, bronchoscopes, ureteroscopes).
Cycle 2—Surface devices with high compatibility with ozone, hinged instruments and rigid endoscopes (1 mm x 50 cm).
Cycle 3—Instruments sterilizable with cycle #1 and complex endoscopes (Ex. gastroscopes, colonoscopes).

Although it is preferred to operate the exemplary sterilization process using a 50% hydrogen peroxide solution, the process can be operated with solutions including 3%-50% hydrogent peroxide. Exemplary conditions for the process when operated with a 3%, 30% and 50% hydrogen peroxide solution are as follows.

TABLE II

| % $H_2O_2$ | Max Injection Pressure (Torr) | Ozone dose (mg/L) | No of repetitions | Conditioning time |
|---|---|---|---|---|
| 3 | 44-54 | 25-50 | 2-8 | 2 hrs |
| 30 | 30-44 | 5-25 | 2-6 | 2 hrs |
| 50 | 17-21 (20) | 2-10 | 2-4 | 0 hr |

The maximum injection pressure is the pressure at which injection of the evaporated hydrogen peroxide solution is stopped. The conditioning time represents a time period after sealing of the chamber and prior to application of the vacuum in which the articles to be sterilized are maintained in the sterilization chamber and gradually warm up from room temperature due to the chamber walls, floor and door being heated to about 40° C. This warming up of the load in the chamber is required to prevent undue condensation of water on the load on injection of the evaporated hydrogen peroxide solution. The risk of condensation increases with decreasing hydrogen peroxide solution concentrations.

Once the user has chosen one of the three cycles, the user closes the sterilization chamber door and pushes the start button. The sterilizer control system (see FIG. 9) will then, under the control of a built in operating software, start the sterilization process according to the cycle chosen and using preselected parameters for the cycle chosen. The cycle starts with the generation of a vacuum in the sterilization chamber of approximately 1 Torr (1.33 mbar). An evaporated aqueous hydrogen peroxide solution is subsequently injected into the chamber through the evaporator unit to partially sterilize and humidify the load. Before entering the evaporator unit, the hydrogen peroxide solution passes through the metering unit 240 shown in FIG. 8. The metering unit 240 is directly connected to the evaporator unit 260 and, thus, subjected to the vacuum pressure present in the chamber. The metering unit 240 includes a base block 241 having a passage of a fixed, known volume (not shown) and connected by an intake valve 242 at an upstream end of the passage to the hydrogen peroxide reservoir 220 and by an exhaust valve 243 at a downstream end of the passage to the evaporator unit 260. The flow of hydrogen peroxide solution through the metering unit 240 can be exactly controlled by way of the valves 242, 243, which are switched oppositely and non-overlapping so that one valve is always closed when the other is open and both valves are never open at the same time. In this manner, the passage is evacuated when the exhaust valve 243 is open and the intake valve 242 is closed, filled with hydrogen peroxide solution when the exhaust valve 243 is closed and the intake valve 242 is open and evacuated again when the exhaust valve 243 is again open and the intake valve 242 is again closed. Since the exact volume of the passage is known, the amount of hydrogen peroxide solution supplied per valve cycle is known and the total amount of hydrogen peroxide can be calculated on the basis of the number of valve switching cycles. The number of times and the frequency that the valves 242, 243 open and close are controlled and monitored by apparatus software and can be used to determine the amount of hydrogen peroxide solution removed from the reservoir and to calculate the theoretically remaining amount of solution in the reservoir, based on the total amount aspirated from the supply bottle and the metered amount.

Figure 2:
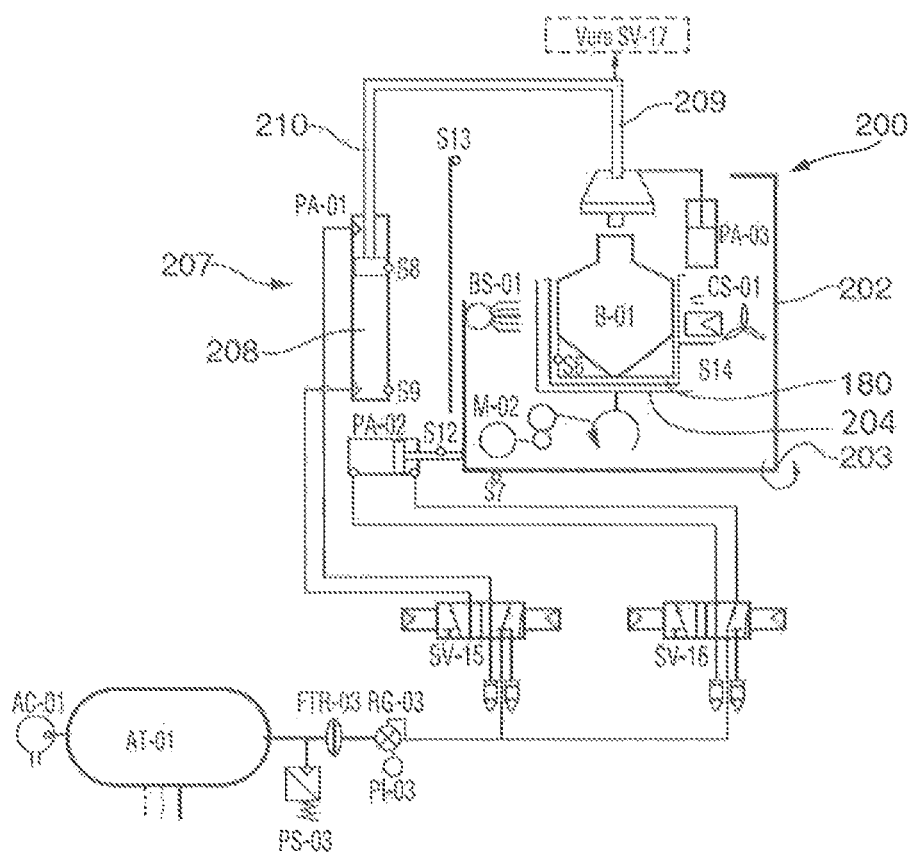
FIG. 2 shows a schematic diagram of a hydrogen peroxide delivery system in accordance with the disclosure, the illustrated parts of the system being listed in Table III.
Figure 7:
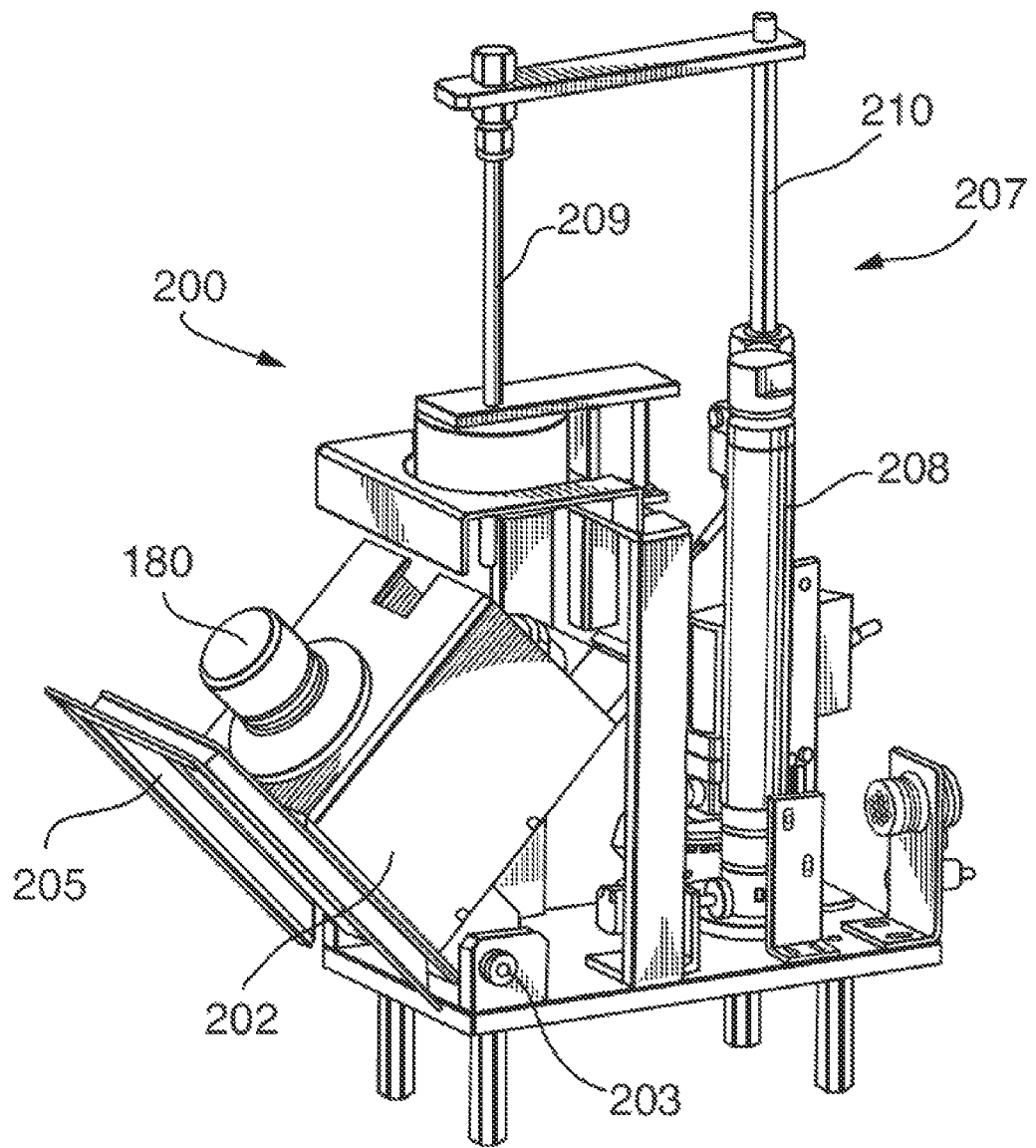
FIG. 7 shows an exemplary embodiment of a hydrogen peroxide supply unit in accordance with the disclosure.

As shown in FIGS. 2 and 7, the hydrogen peroxide delivery system 200 of this disclosure intended for a sterilizer having a hydrogen peroxide injection unit and a housing, includes a bottle holder or cradle 202 for supporting a sealed hydrogen peroxide solution container 180 in an upright position within the housing (not shown), a drainage arrangement 207 connected with the cradle for aspirating the hydrogen peroxide solution from the container 180, and a delivery arrangement connected with the drainage arrangement for supplying the aspirated hydrogen peroxide solution to the hydrogen peroxide injection unit. The drainage arrangement 207 includes a drainage needle 209 connected with the delivery arrangement for penetrating a seal on the container 180 and extending into the hydrogen peroxide solution in the container, and a needle drive 208 for moving the needle from an at rest position, wherein the needle is retracted to allow insertion of a new hydrogen peroxide container into the cradle, to a penetrating position wherein the needle penetrates the seal of the container and extends into the hydrogen peroxide solution in the container. In the penetrating position, the needle preferably extends all the way to a bottom of the container.

In a preferred embodiment, the delivery system includes a bottle holder 202 for receiving a sealed hydrogen peroxide solution bottle 180. The holder has a bottle seat or cradle 204 in which the bottle 180 is fittingly received. The bottle 180, which will be discussed in more detail further below, is held in the seat 204 by gravity only. The holder 202 is rotatably mounted on pivot 203 for movement between an open position as illustrated in FIG. 7, which the bottle 180 can be placed into or removed from the holder and a closed position in which the holder is completely within the sterilizer cabinet or housing (not shown) and a front cover 205 of the holder closes off all access to the holder from outside the cabinet. When the holder 202 is in the closed position, a pneumatically driven drainage arrangement 207, including a needle drive, in this embodiment a vertically oriented pneumatic cylinder 208, and a drainage needle 209 mounted on the piston rod 210 of the cylinder, is activated to drain all hydrogen peroxide solution from the bottle 180. This is achieved by activating the cylinder 208 to force needle 209 through the bottle seal until the needle tip reaches the bottom of the bottle 180. The needle 209 is fluidically connected to the reservoir 240 (see FIG. 8) and the solution is aspirated from the bottle 180 and into reservoir 240 by using the vacuum generated by the vacuum pump 44 to which the reservoir 240 can be fluidically connected by conduit 211 and valve 212 (see FIG. 1). Once the contents of the bottle 180 have been aspirated, the holder can be opened and the bottle removed, or the empty bottle can be kept in the holder until a refill of the reservoir 240 is required. The reservoir 240 is provided with a level sensor 242 which provides a signal to the control system on the liquid level in the reservoir. Based on the signal received from the sensor 242, the control system notifies the user if the amount of liquid in the reservoir 240 is insufficient for the execution of the cycle selected by the user.

In an alternate embodiment, the hydrogen peroxide delivery system does not include a reservoir. Instead, the bottle 180 itself is cooled down (CS-01) to avoid rapid degradation of the aqueous hydrogen peroxide. An ultrasonic sensor (S14) measures the amount of solution left in the bottle. When the solution reaches a $1^{st}$ preselected level, a $1^{st}$ warning appears on the screen and when a lower, $2^{nd}$ preselected level is reached, the message generated from the software to the operator specifies that only one more sterilization cycle #1 or #2 can be run with the remaining solution in the bottle. The operator will then have to reload the delivery system with a fresh, full bottle.

As shown in FIGS. 10*a* to 10*d*, the bottle 180 has a conical bottom 182 to ensure a complete drainage of all liquid in the bottle, thereby reducing the danger of spills or contamination on removal of a drained bottle. In order to ensure the bottle 180 securely remains upright, a stand 184 is attached to the bottom end of the bottle. The stand 184 includes an upturned cup 185 snap fitted into a circumferential groove 186 on the bottle exterior wall 187. The needle 209 is aligned with the lowest point in the bottle bottom and can be moved into the bottle, through the bottle seal, until it reaches the lowest point in the bottle. Mechanical, electronic or other control structures and functions are provided to ensure contact of the needle with the bottle bottom while preventing penetration of the bottle bottom. The control structures may include a force sensor S9 for detecting engagement of the needle with the container bottom and terminating needle advance by the needle drive PA01 to avoid penetration of the container bottom by the needle. The force sensor is preferably incorporated into the needle drive and/or the needle mount (not shown).

In the preferred embodiment, the needle drive is reciprocatable for moving the needle back and forth between the at rest and penetrating positions, whereby in the at rest position the needle is retracted to allow insertion of a new hydrogen peroxide container and in the penetrating position the needle penetrates the seal of the container and extends into the hydrogen peroxide solution in the container all the way to the bottom of the container.

H2O2 Dispensing System Control Processing

Figure 8:
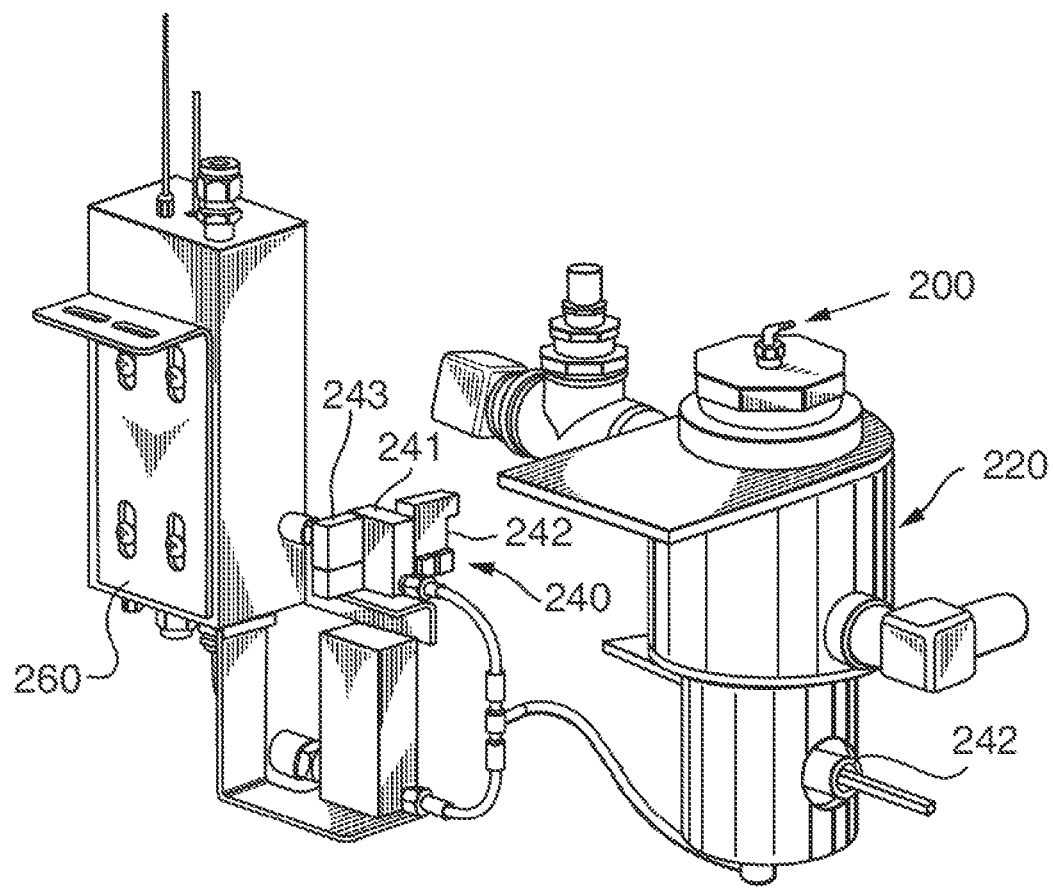
FIG. 8 shows an exemplary embodiment of a hydrogen peroxide reservoir, metering and evaporation assembly.
Figure 9A:
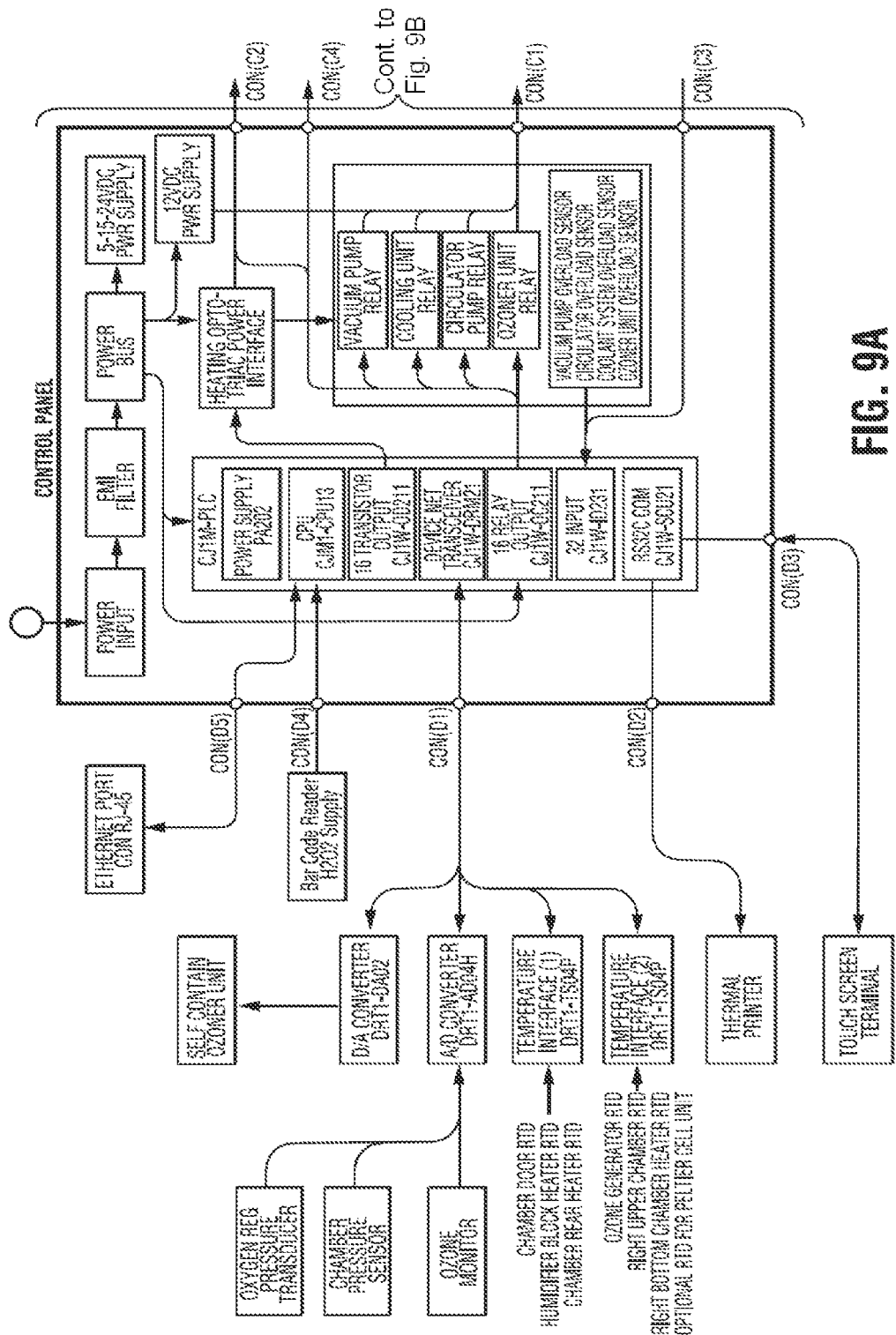
Figure 9B:
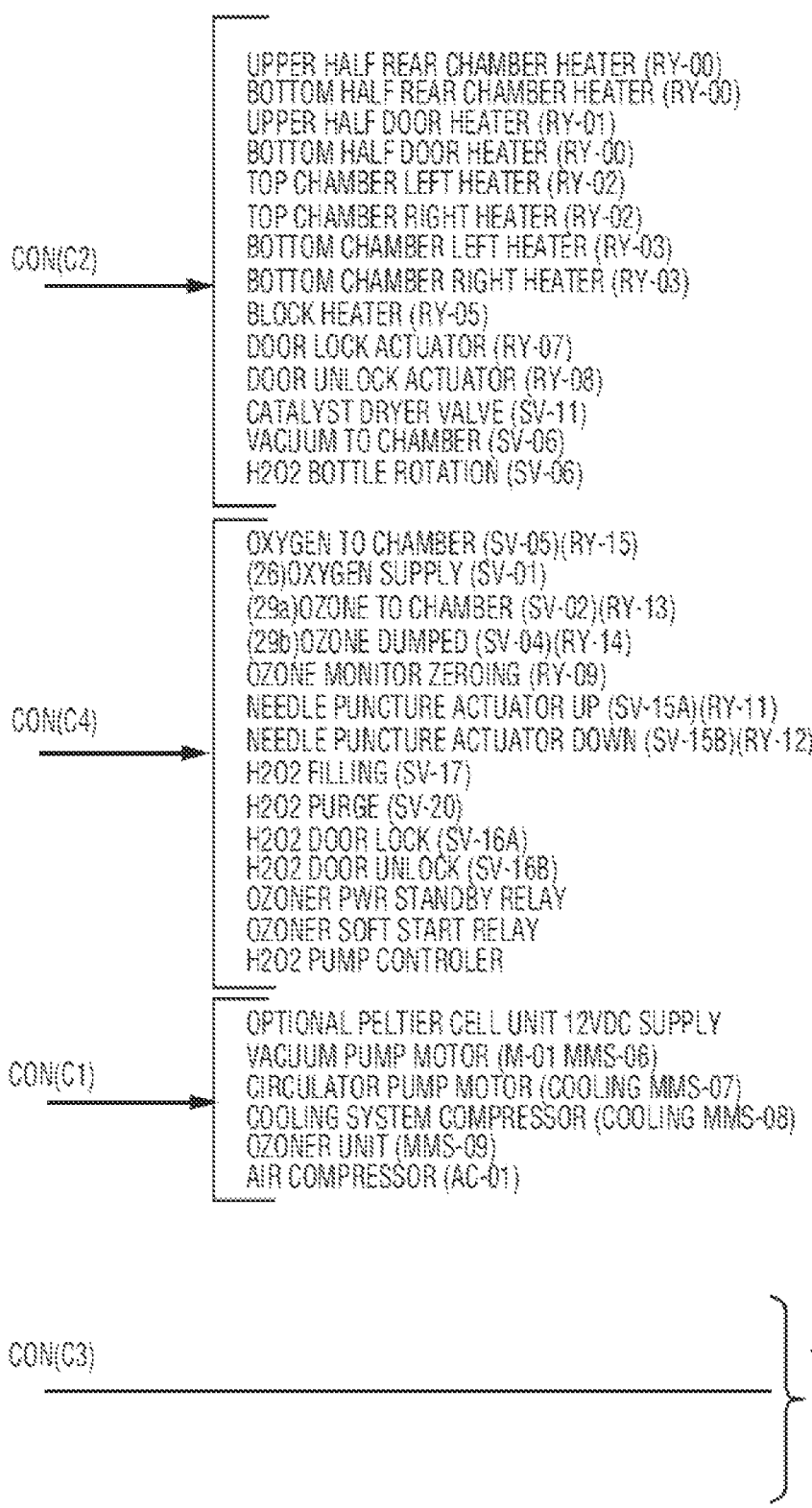
Figure 10A:
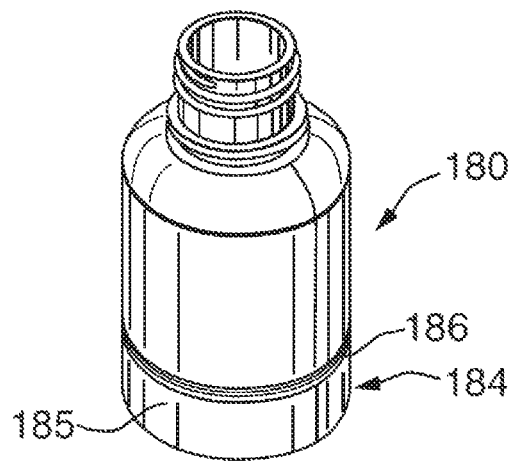
FIG. 10a is a perspective view of a sterilant container in accordance with the invention.
Figure 10B:
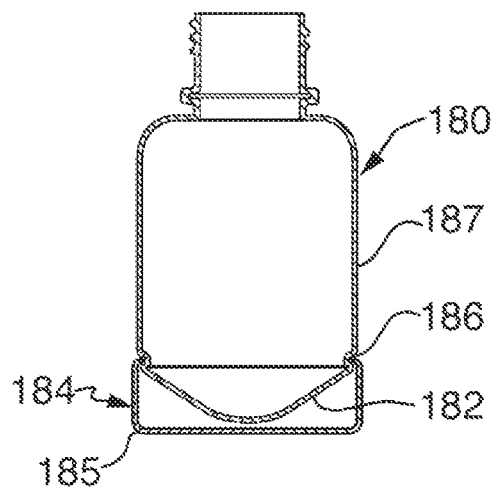
Figure 10C:
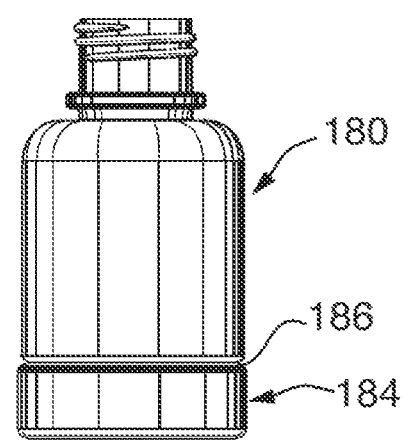
Figure 10D:
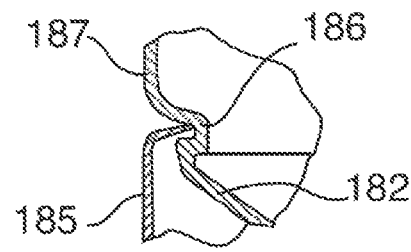
FIG. 10d is enlarged detail B of the container shown in FIG. 10b.

At the moment, two configurations of an H2O2 dispensing system are possible. The control system could be used for both systems. The first system depicted in the present application in FIG. 7 and FIG. 8 is mainly a bottle of H2O2 (180) flushed into a temperature controlled reservoir (240) FIG. 8. This first system will be described with reference to FIGS. 7,8,9 and 2. All input and output sensors described in the following appear in the list of inputs and outputs of the control system listed on FIG. 9. When the strerilizer is first initialized, the door 12 is closed and the closed position is sensed by switch S7. No bottle is sensed in the holder by (S6), the puncture needle is also retracted to the up position by the cylinder PA-01 (208). S8 and S9 provide sensing for the upward and downward position of cylinder (208). Also, actuator PA-02 is retracted in the holder unlocked position. The user is invited by the message on the screen (118) to open the door (205) and to insert a H2O2 bottle in the holder. So when the bottle is sensed by S6, another message on the screen (118) invites the user to close the door (205) which is sensed by S7. Software control is carried out by the CPU (108) and condition sensors. The bottle is set by gravity on a rotating base (209). The CPU starts the motor M-02 to rotate the bottle 180. A bar code reader BS-01 (FIG. 2,) (122) FIG. 9 reads a bar code on the bottle. The CPU verifies the expiry date of the bottle and if the bottle is past its expiry date, the door 205 remains unlocked and a message on the screen (118) invites the user to change the bottle for another one. If the date is correct, the CPU stops the motor M-02 and locks the door (205) by actuating PA-02 (FIG. 2). Then CPU actuates the cylinder (208) for the needle 209 to perforate the sealed cap of the bottle until S9 senses the needle in the down position. Then the bottle is totally emptied into the reservoir 240 by suction provided through valve (212) and vacuum from pump (40). The door (205) remains locked until all the H2O2 in the reservoir has been used. Level sensors S10 and S11 provide the conditions necessary for the CPU to estimate if another bottle is needed. If so, the needle is retracted from the bottle and the door (205) is unlocked and the user is invited by a message on the screen (118) to replace the H2O2 bottle.

Description of the Alternate and Preferred H2O2 Dispensing System

The following dispensing system does not include the cooled reservoir (240). Instead, the H2O2 remains in the bottle (180). Level detectors S10 and S11 are removed and replaced by the ultrasonic level detector S14 which is spring loaded against a side of the bottle near the bottom and used as a low level detector to indicate to the CPU an empty bottle. Because this sensor is spring loaded, it adds too much friction on the bottle to use the motor M-02. Therefore, the user is invited by a message on the screen (118) to rotate the bottle manually until the bar code is read by (BS-01) FIG. 2 or (122) FIG. 9. If the bottle is not out of date, the user is invited to close the door (205) and the CPU locks the compartment of the bottle holder and actuates (208) to puncture down the needle. In that preferred embodiment, the H2O2 holder is temperature controlled by a Peltier cell unit. An RTD attached to the holder and connected to the temperature interface (121) sends data to the CPU (108) by Device Net network and the CPU controls by PID function the amount of power being applied to the Peltier cell unit. The Peltier unit is supplied by the 12 VDC (121) power supply used also for the air compressor driving the pneumatic system composed of SV-15, SV-16, actuators (PA-02 and PA-01) on FIG. 2. Between each cycle, the line connected between the H2O2 bottle (180) and micro valve module (240) will be purged by SV20. Near the inlet of module (240) a foam optical detector snapped on the H2O2 line will indicate the total refill of the line without air in the line.

To that point both H2O2 dispensing systems can supply the micro valves module (240). The micro valves (SV-18 and SV19) are working reciprocally for a preset duty cycle program on an on board microcontroller circuit generating the proper timing pulses for both micro-valves. That electronic circuit is activated by a signal from the CPU (108) called H2O2 pump controller signal FIG. 9. Under software control, a proper amount of H2O2 is allowed in the humidifier manifold (260, FIG. 1). This manifold is temperature controlled by the CPU (108) using data of RTD (TT-04, FIG. 1) and controlling heater HTR-01 (FIG. 1) by PID function. Then the H2O2 vaporizes in the manifold (260) and the vapor is sent to the chamber under vacuum through pipe (280, FIG. 1).

In the preceding description, for purposes of explanation, numerous details are set forth in order to provide a thorough understanding of the embodiments of the invention. However, it will be apparent to one skilled in the art that these specific details are not required in order to practice the invention. In other instances, well-known sterilizer structures and circuits are shown in block diagram or symbol form in order not to obscure the invention. For example, specific details are not provided as to whether certain parts of the sterilizer controls are implemented as a software routine, hardware circuit, firmware, or a combination thereof.

The above-described embodiments of the invention are intended to be examples only. Alterations, modifications and variations can be effected to the particular embodiments by those of skill in the art without departing from the scope of the invention, which is defined solely by the claims appended hereto.

TABLE III

| Oxygen Circuit | |
|---|---|
| FTR-01 | Oxygen Inlet Filter |
| RG-01 | Oxygen Pressure Regulator |
| SV-01 | Oxygen Supply Valve |
| PS-01 | Oxygen Pressure Switch |
| FI-01 | Oxygen Flow Indicator |
| SV-05 | Oxygen To Chamber Valve |
| Ozone Circuit | |
| | Ozone Generator |
| TT-01 | Temperature Transmitter for Ozone Generator Cooling |
| AOZ-01 | Ozone Monitor |
| | Orifice (used to regulate ozone flow to chamber) |
| SV-02 | Ozone To Chamber Valve |
| SV-04 | Ozone Dumped Valve (By-pass) |
| Air Circuit | |
| AC-01 | Air compressor |
| AT-01 | Compressed air tank |

TABLE III-continued

| | |
|---|---|
| PS-03 | Pressure switch for air compressor |
| RG-03 | Air pressure regulator |
| PI-03 | Air Pressure indicator |
| FTR-03 | Air inlet filter |
| | Aluminium Block |
| TT-04 | Aluminium Block Temperature Transmitter |
| HTR-01 | Heating Element |
| | STERIZONE Solution Circuit |
| SV-17 | $H_2O_2$ filling valve |
| SV-21 | $H_2O_2$ vent valve |
| SV-18 | $H_2O_2$ inlet valve |
| SV-19 | $H_2O_2$ outlet valve |
| SV-20 | $H_2O_2$ purge valve |
| | STERIZONE Solution Supply System |
| S6 | Sensor (detects STERIZONE Solution container presence-absence status) |
| S7 | Sensor (detects STERIZONE Solution compartment open-close status) |
| S8 | Sensor (detects PA-01 upper position) |
| S9 | Sensor (detects PA-01 lower position) |
| S12 | Sensor (detects STERIZONE Solution compartment locked-unlocked status) |
| S13 | Sensor (detects STERIZONE Solution compartment access (fascia) opened-closed status) |
| S14 | Sensor (detects the lower level of $H_2O_2$ in the bottle) |
| S15 | Sensor (detects presence of air bubble in the line) |
| SV-15 | Air pilot valve for needle puncture actuators |
| | PM-900-014 |
| SV-16 | Air pilot valve for STERIZONE Solution compartment lock actuator |
| B-01 | Custom taper shape bottom STERIZONE Solution bottle |
| BS-01 | Barcode scanner for bottle |
| PA-01 | Pneumatic actuator for bottle puncture |
| PA-02 | Pneumatic actuator for STERIZONE Solution compartment lock |
| PA-03 | Pneumatic actuator for puncture needle centering |
| M-02 | Electric motor that rotate bottle for barcode scanning |
| CS-01 | Cooling system for the bottle |
| VS-02 | Vacuum switch (to fill and purge $H_2O_2$ line) |
| | Sterilization Chamber |
| S1 | Door Closed Upper Switch |
| S2 | Door Closed Lower Switch |
| S4 | Door Locked Switch |
| S3 | Door Unlocked Switch |
| PT-01 | Chamber Pressure Transmitter |
| VS-01 | Chamber Vacuum Switch |
| TT-03,5,6 | Chamber Temperature Transmitters |
| TT-07 | Chamber Door Temperature Transmitter |
| | Vacuum Circuit |
| SV-06 | Chamber Vacuum Valve |
| M-01 | Vacuum Pump Run status flag |
| M-01 | Vacuum Pump Contactor |
| CAT-01 | Catalytic Converter |
| | Catalyst Drying Circuit |
| FTR-02 | Port muffler |
| SV-11 | Air to Catalytic Converter Valve (Catalyst Dryer Valve) |
| | PM-900-002 |
| | Cooling Circuit |
| FS-02 | Coolant Flow Switch |
| M-05 | Circulation Pump Run status flag |
| M-05 | Circulation Pump Contactor |
| | Overload Circulation Pump |
| PS-02 | Compressor Low Pressure Switch |
| M-06 | Compressor Run status flag |
| M-06 | Compressor Contactor |
| | Overload Compressor |

The invention claimed is:

1. A hydrogen peroxide sterilizer, comprising a sterilization chamber and a hydrogen peroxide delivery system with a hydrogen peroxide injection unit for injection of hydrogen peroxide into the sterilization chamber and a housing, the delivery system including a cradle for fittingly supporting a sealed hydrogen peroxide solution container in an upright position within the housing, the container having a hollow container body with a top end including a sealed fill and drainage opening, a side wall and an outwardly conical bottom to ensure any residual hydrogen peroxide solution collects at a lowest point of the container bottom;

a drainage arrangement connected with the cradle for aspirating the hydrogen peroxide solution from the container, and connected to the hydrogen peroxide injection unit for supplying the aspirated hydrogen peroxide solution to the hydrogen peroxide injection unit, the drainage arrangement including a drainage needle for penetrating a seal on the sealed fill and drainage opening of the container and extending into the hydrogen peroxide solution in the container, the cradle supporting the container for aligning the lowest point in the container bottom with an axis of the needle, and a pneumatic needle drive for moving the needle along the needle axis from an at rest position, wherein the needle is retracted to allow insertion of a new hydrogen peroxide container into the cradle, to a penetrating position wherein the needle penetrates the seal of the container and extends in the hydrogen peroxide solution in the container all the way to the lowest point in the container bottom; and a control structure incorporated into the needle drive for ensuring contact of the needle with the lowest point of the container bottom in the penetrating position while preventing penetration of the container bottom by the needle.

2. The sterilizer of claim 1, wherein the needle drive is reciprocal for moving the needle back and forth between the at rest and penetrating positions.

3. The sterilizer of claim 1, wherein the control structure includes a force sensor for detecting engagement of the needle with the container bottom and terminating needle advance by the needle drive to avoid penetration of the container bottom by the needle.

4. The sterilizer of claim 3, wherein the force sensor is incorporated in the needle drive.

5. The sterilizer of claim 1, further comprising an ultrasonic sensor for detecting when the hydrogen peroxide liquid in the container drops below a predetermined level.

6. The sterilizer of claim 5, wherein the container is supported on a stand and the ultrasonic sensor is spring biased against the container, when the container is supported on the stand.

7. The sterilizer of claim 1, wherein the sealed hydrogen peroxide solution container further comprises a stand for maintaining the container in an upright position on a flat horizontal surface prior to insertion into the cradle and a connecting arrangement for connecting the stand to the body.

8. The sterilizer of claim 7, wherein the container includes an external circumferentially extending, continuous groove in the side wall of the body and the stand is cup-shaped and has at least two radially inwardly extending tabs for engagement with the groove to provide a snap fit connection of the stand to the body.

9. The sterilizer of claim 8, wherein each tab is a circumferentially extending flange at a top end of the stand for snap fit engagement with the groove.

10. A hydrogen peroxide sterilizer, comprising a sterilization chamber and a hydrogen peroxide delivery system with a hydrogen peroxide injection unit for injection of hydrogen peroxide into the sterilization chamber and a housing, the delivery system including
- a cradle for fittingly supporting a sealed hydrogen peroxide solution container in an upright position within the housing,
- a sealed hydrogen peroxide solution container in the cradle;
- a drainage arrangement connected with the cradle for aspirating the hydrogen peroxide solution from the container, and
- connected to the drainage arrangement for supplying the aspirated hydrogen peroxide solution to the hydrogen peroxide injection unit, the sealed hydrogen peroxide solution container having a hollow container body with a top end including a sealed fill and drainage opening, side wall and an outwardly conical bottom to ensure any residual hydrogen peroxide solution collects at a lowest point of the container bottom; and
- the drainage arrangement including a drainage needle for penetrating the sealed drainage opening and extending into the hydrogen peroxide solution in the container, the cradle supporting the container for aligning the lowest point in the container bottom with an axis of the needle, and a pneumatic needle drive for moving the needle along the needle axis from an at rest position, wherein the needle is retracted to be clear of the sealed drainage opening, to a penetrating position wherein the needle penetrates the sealed drainage opening and extends in the hydrogen peroxide solution in the container, all the way to the lowest point in the container bottom; and
- a control structure incorporated into the needle drive for ensuring contact of the needle with the lowest point of the container bottom in the penetrating position while preventing penetration of the container bottom by the needle.

11. The delivery system of claim 10, wherein the container further includes a stand for maintaining the container in an upright position on a flat horizontal surface prior to insertion into the cradle and a connecting arrangement for connecting the stand to the container body.

12. The delivery system of claim 11, wherein the side wall of the container body includes an external, circumferentially extending, continuous groove and the stand is cup-shaped and has at least a pair of radially inwardly extending tabs for engagement with the groove to provide a snap fit connection of the stand to the body.

13. The delivery system of claim 12, wherein each tab on the stand is a circumferentially extending flange at a top end of the stand for snap fit engagement with the groove.

14. A hydrogen peroxide sterilizer, comprising a sterilization chamber and a hydrogen peroxide delivery system with a hydrogen peroxide injection unit for injection of hydrogen peroxide into the sterilization chamber and a housing, the delivery system including
- a cradle for fittingly supporting a sealed hydrogen peroxide solution container in an upright position within the housing, the container having a hollow container body with a top end including a sealed fill and drainage opening, a side wall and an outwardly conical bottom to ensure any residual hydrogen peroxide solution collects at a lowest point of the container bottom;
- a drainage arrangement connected with the cradle for aspirating the hydrogen peroxide solution from the container, and connected to the hydrogen peroxide injection unit for supplying the aspirated hydrogen peroxide solution to the hydrogen peroxide injection unit, the drainage arrangement including a drainage needle for penetrating a seal on the container and extending into the hydrogen peroxide solution in the container, the cradle supporting the container for aligning the lowest point in the container bottom with an axis of the needle, and a needle drive for moving the needle along the needle axis from an at rest position, wherein the needle is retracted to allow insertion of a new hydrogen peroxide container into the cradle, to a penetrating position wherein the needle penetrates the seal of the container and extends in the hydrogen peroxide solution in the container all the way to the lowest point in the container bottom; and
- a control structure incorporated into the needle drive for ensuring contact of the needle with the lowest point of the container bottom in the penetrating position while preventing penetration of the container bottom by the needle.

15. The delivery system of claim 14, wherein the needle drive is reciprocal for moving the needle back and forth between the at rest and penetrating positions.

16. The delivery system of claim 14, wherein the control structure includes a force sensor for detecting engagement of the needle with the container bottom and terminating needle advance by the needle drive to avoid penetration of the container bottom by the needle.

17. The delivery system of claim 16, wherein the force sensor is incorporated in the needle drive.

18. The delivery system of claim 14, further comprising an ultrasonic sensor for detecting when the hydrogen peroxide liquid in the container drops below a predetermined level.

19. The delivery system of claim 18, wherein the container is supported on a stand and the ultrasonic sensor is spring biased against the container, when the container is supported on the stand.

20. The delivery system of claim 14, wherein the sealed hydrogen peroxide solution container further comprises a stand for maintaining the container in an upright position on a flat horizontal surface prior to insertion into the cradle and a connecting arrangement for connecting the stand to the body.

21. The delivery system of claim 20, wherein the container includes an external circumferentially extending, continuous groove in the side wall of the body and the stand is cup-shaped and has at least two radially inwardly extending tabs for engagement with the groove to provide a snap fit connection of the stand to the body.

22. The delivery system of claim 21, wherein each tab is a circumferentially extending flange at a top end of the stand for snap fit engagement with the groove.

* * * * *